United States Patent
Winkler et al.

(10) Patent No.: US 6,827,142 B2
(45) Date of Patent: Dec. 7, 2004

(54) PROCESS AND APPARATUS FOR ACHIEVING PRECISION TEMPERATURE CONTROL

(75) Inventors: Gary Winkler, St. Louis, MO (US); Jere Poteat, Leslie, MO (US)

(73) Assignee: Innoventor Engineering, Inc., Chesterfield, MO (US)

( * ) Notice: Subject to any disclaimer, the term of this patent is extended or adjusted under 35 U.S.C. 154(b) by 80 days.

(21) Appl. No.: 09/844,072

(22) Filed: Apr. 27, 2001

(65) Prior Publication Data

US 2002/0020179 A1 Feb. 21, 2002

Related U.S. Application Data

(60) Provisional application No. 60/201,848, filed on Apr. 27, 2000.

(51) Int. Cl.[7] .............................................. G05D 23/00
(52) U.S. Cl. ...................................... 165/298; 165/247
(58) Field of Search ................................. 165/298, 247, 165/80.4

(56) References Cited

U.S. PATENT DOCUMENTS

| | | | | | |
|---|---|---|---|---|---|
| 5,226,471 A | * | 7/1993 | Stefani | ................... | 165/80.4 X |
| 5,623,990 A | * | 4/1997 | Pirkle | .......................... | 165/298 |
| 6,449,969 B1 | * | 9/2002 | Fujimoto et al. | ....... | 165/247 X |

* cited by examiner

Primary Examiner—Ljiljana Ciric
(74) Attorney, Agent, or Firm—Armstrong Teasdale LLP (57) ABSTRACT

An apparatus providing effective control of fluid temperature to achieve temperature control precision of ±0.1° F. at flow rates exceeding five gallons/minute includes a hot and a cold reservoir of process fluid maintained at their desired temperatures by a high-accuracy industrial chiller and an industrial heater, respectively. A control valve mixes fluid from the reservoirs to produce a precisely controlled stream of process fluid delivered to the point of usage. Another flow control valve maintains system flow at a precise value.

16 Claims, 6 Drawing Sheets

PROCESS AND APPARATUS FOR ACHIEVING PRECISION TEMPERATURE CONTROL

CROSS REFERENCE TO RELATED APPLICATIONS

This application claims the benefit of U.S. Provisional Application No. 60/201,848, filed Apr. 27, 2000, which is hereby incorporated by reference in its entirety.

BACKGROUND OF THE INVENTION

This invention relates generally to apparatus and methods for process temperature control, and more particularly, to apparatus and methods for controlling process temperature with high precision.

Many processes require precise temperature control of cooling loops. This precision is critical for medical lasers and other electronic equipment where essential parameters such as frequency are affected by changes in temperature. For certain applications, minor variance in temperature-dependent properties has a detrimental effect.

High-accuracy techniques exist for low flow rates, under approximately 5 gallons per minute (gpm). One such method utilizes solenoid valves for hot and cold sources that open alternately at a high frequency to allow the hot and cold fluid to mix. A temperature sensor reports the mixed temperature to a temperature controller that compares the input signal from the temperature sensor with the controller's setpoint temperature to determine the average time each valve is open.

Typical industrial chillers can control to approximately $\pm 10°$ F. High-precision industrial chiller technology exists to control to approximately $\pm 1°$ F. This precision is sufficient for most industrial applications, but does not meet the requirements of the applications mentioned above. It would be desirable to provide apparatus and methods to control to approximately $\pm 0.1°$ F., thus providing stability for temperature-critical systems and components.

BRIEF SUMMARY OF THE INVENTION

In an exemplary embodiment of the invention, an apparatus includes a hot and a cold reservoir of process fluid maintained at their desired temperatures by a high-accuracy industrial chiller and an industrial heater, respectively. A three-way control valve mixes fluid from the reservoirs to produce a precisely controlled stream of process fluid delivered to the point of usage. Another flow control valve maintains system flow at a precise value.

In another embodiment, a heat exchanger upstream of the point of usage removes heat from the process stream, and in a further embodiment returns the process fluid to a reservoir with a temperature at or above the desired final temperature. Temperature control of the cooling water supplied to the heat exchanger results from a high-accuracy industrial chiller, and, in one embodiment, a reservoir on the cooling side. A two-way control valve modulates the amount of cooling water flowing through the heat exchanger, producing the final precisely-controlled fluid stream on the process side. Another flow control valve maintains system flow at a precise value.

In a further embodiment, the invention includes a pair of two-way valves to control the mixing of fluid from a hot and a cold reservoir to produce the final precisely-controlled fluid stream delivered to the point of usage. The cold and hot reservoirs are maintained at their desired temperatures by a high-accuracy industrial chiller and by an industrial heater, respectively. Another flow control valve maintains system flow at a precise value.

In yet another embodiment, the invention comprises a single reservoir of process fluid maintained slightly below the desired final temperature to be delivered to the point of usage by a high-accuracy industrial chiller. Immediately prior to the point of usage, a two-way control valve diverts a portion of the fluid through a heater loop maintained at its desired temperature by a programmable temperature controller. Another flow control valve maintains system flow at a precise value.

In a still further embodiment, refrigerant in the vapor phase is compressed and passed through an economizing heat exchanger, where it is cooled by the returning saturated vapor refrigerant. The cooled refrigerant vapor passes through an expansion valve, where most of it returns to the liquid phase, and then passes into a phase separator tank. Liquid refrigerant is pumped to the point of usage, where the heat input vaporizes the refrigerant. The refrigerant then passes back to the phase separator. Vapor from the separator then travels through the previously mentioned heat exchanger and back to the compressor inlet.

DETAILED DESCRIPTION OF THE INVENTION

Figure 1:
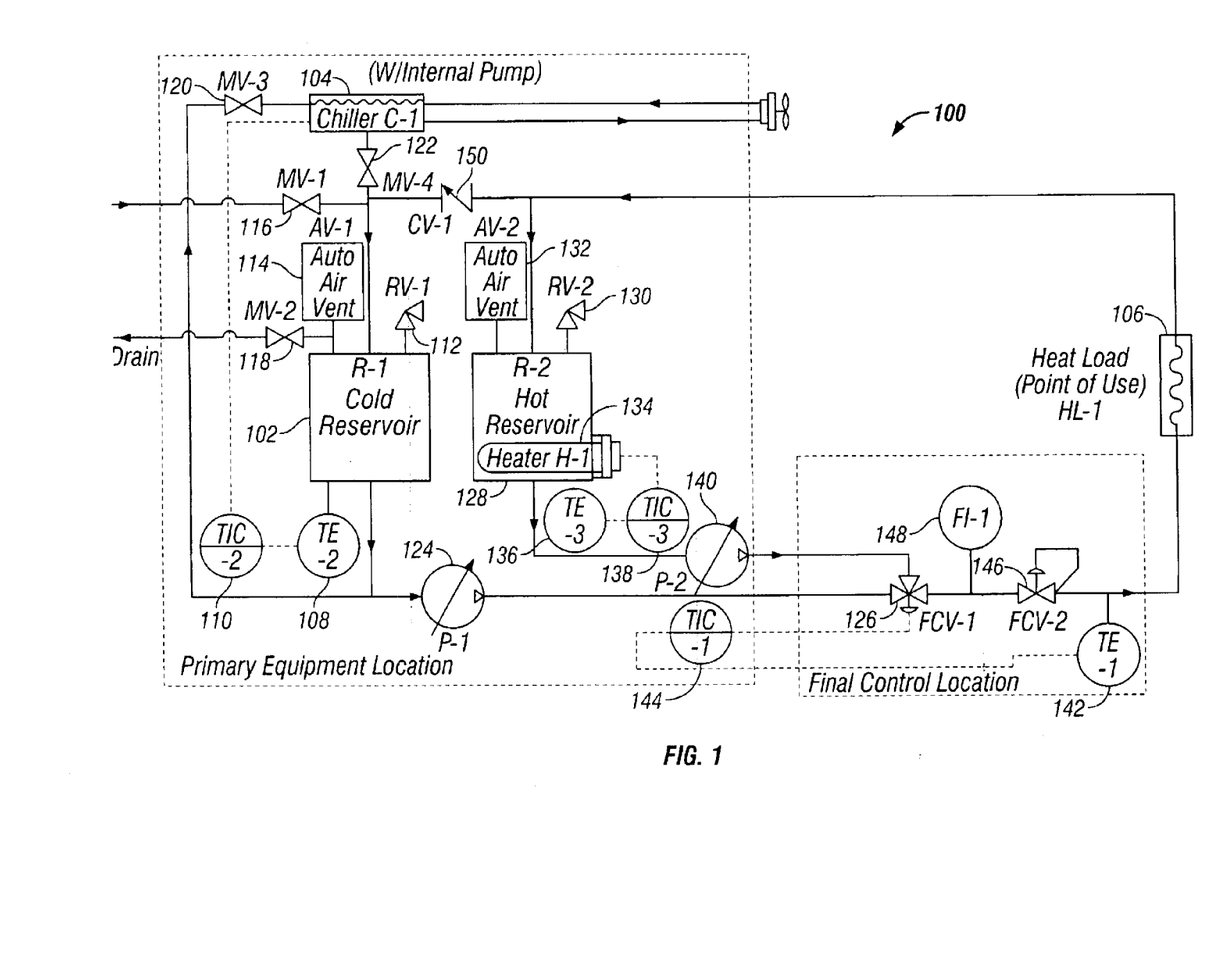
FIG. 1 is a schematic illustration of a temperature control apparatus including single valve fluid mixing.

FIG. 1 is a schematic illustration of a temperature control apparatus 100 for achieving precision temperature control of fluids, for example, $\pm 0.1°$ F. at flow rates exceeding 5 gallons/minute. A cold reservoir 102 contains fluid that is maintained slightly (for example 2° F.) below the final temperature setpoint by a chiller 104. Final temperature setpoint is defined as the temperature desired at a heat load 106. A temperature sensor 108 senses the temperature of cold reservoir 102 and feeds the value to a chiller temperature controller 110. Temperature controller 110 compares its setpoint to the value returned by sensor 108, and controls the amount of cooling provided by chiller 104. Chiller 104 has an internal pump that circulates fluid through cold reservoir 102.

In one embodiment, cold reservoir 102 is equipped with a relief valve 112 to protect from overpressure, and with an automatic air vent 114 to vent excess air. Cold reservoir 102 is sized to provide thermal inertia for the system, which is utilized to precisely control the final temperature. Additionally, apparatus 100 includes manual valves 116, 118, 120, and 122. Valves 116 and 118 are normally closed, while valves 120 and 122 are normally open. These settings are reversed if facility backup cooling is used. A variable displacement pump 124 draws fluid from cold reservoir 102 and delivers it to a first three-way control valve 126. In an alternative embodiment, a recirculation loop (not shown) to prevent pump overheating, and a circulation pump (not shown) to reduce thermal stratification within cold reservoir 102 are included in apparatus 100.

A hot reservoir 128 includes a relief valve 130 to vent any overpressure, and an automatic air vent 132 to vent excess air. Hot reservoir 128 is sized to provide an appropriate amount of thermal inertia for the system. Hot reservoir 128 contains fluid that is maintained above (for example 13° F.) the final temperature setpoint by a heater 134. A temperature sensor 136 senses the temperature of hot reservoir 128 and feeds the value to heater temperature controller 138. Temperature controller 138 compares its setpoint to the value it receives from sensor 136, and from the comparison determines the amount of heating provided by heater 134. A variable displacement pump 140 draws fluid from hot reservoir 128 and delivers it to first three-way control valve 126. In an alternative embodiment, a recirculation loop (not shown) to prevent pump overheating, and a circulation pump (not shown) to reduce thermal stratification within hot reservoir 128 are included in apparatus 100. In a further alternative embodiment, variable displacement pump 124 and variable displacement pump 140 are replaced by a single pump (not shown) located downstream of first three-way control valve 126.

A temperature sensor 142 senses the temperature of fluid being delivered to heat load 106, and feeds the value to a final temperature controller 144. Final temperature controller 144 compares its setpoint to the value returned by sensor 142, and controls the position of first three-way control valve 126, which determines the mixing ratio of fluid from hot reservoir 128 and cold reservoir 102.

A second three-way flow control valve 146 regulates system fluid flow at the desired flow rate. Second three-way flow control valve 146 is a pressure-compensated flow-control valve, which internally regulates flow rate independent of system pressure changes. In an alternative embodiment, valve 146 is a standard two-way control valve controlled by an electronic flow controller, through use of a signal from a flow meter. Flow meter 148 displays the fluid flow rate. If second three-way flow control valve 146 is a pressure-compensated flow-control valve as depicted in FIG. 1, then flow meter 148 may be a mechanical meter with visual indication only.

Fluid at the desired temperature and flow rate passes to heat load 106, which raises the temperature of the fluid (assuming the heat load is energized). The fluid then returns to cold reservoir 102 and hot reservoir 128, with flow of chilled fluid into hot reservoir 128 prevented if necessary by check valve 150.

Figure 2:
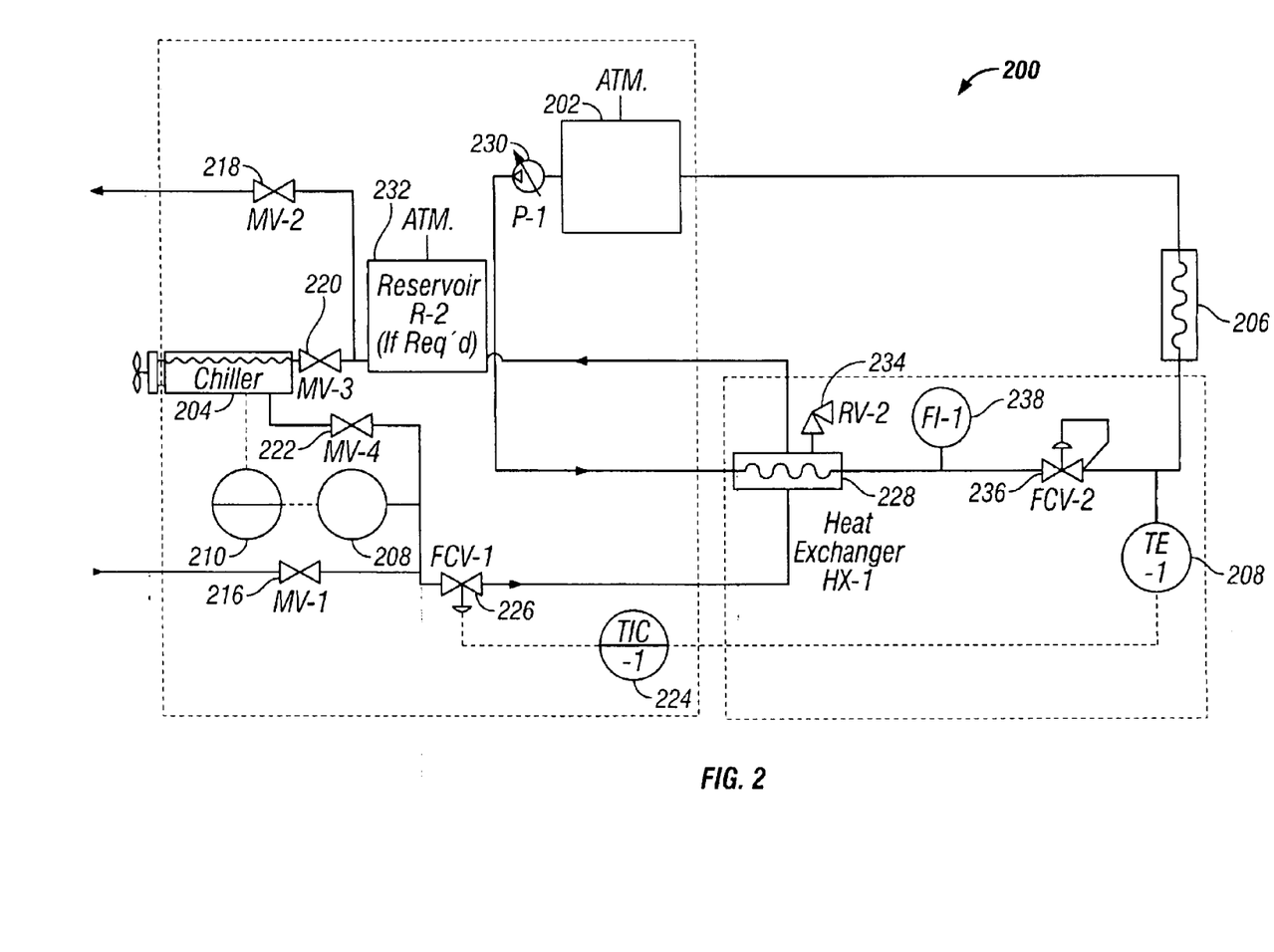
FIG. 2 is a schematic illustration of a temperature control apparatus including a heat exchanger.

FIG. 2 is a schematic illustration of a temperature control apparatus 200 that operates through use of a heat exchanger. In one embodiment, temperature control apparatus 200 includes a system reservoir 202, which contains most of the system's fluid, and also a circulation pump to reduce thermal stratification within system reservoir 202. The temperature of system reservoir 202 depends on the amount of heat that heat load 206 has added to the system recently.

A temperature sensor 208 senses the temperature of fluid exiting chiller 204 and feeds the value to a chiller temperature controller 210. Chiller temperature controller 210 compares its setpoint to the value returned by sensor 208, and controls the amount of cooling provided by chiller temperature controller 210. An internal pump in chiller temperature controller 210 circulates fluid through the cooling loop.

A pair of manual valves 216 and 218 are normally closed, and a pair of manual valves 220 and 222 are normally open, unless facility backup cooling is used, in which case these settings are reversed. In alternative embodiment, valves 216, 218, 220, and 222 are not utilized and sensor 208 is located in reservoir 232.

Temperature sensor 208 senses the temperature of fluid being delivered to heat load 206, and feeds the value to a final temperature controller 224. Temperature controller 224 compares its setpoint to the value returned by temperature sensor 208, and controls the position of a three-way control valve 226, which determines the amount of chilled fluid flowing through the cold side of a heat exchanger 228.

A pump 230 draws fluid from a reservoir 202 and delivers it through heat exchanger 228, where it is cooled to the required temperature. A relief valve 234 protects heat exchanger 228 from overpressure.

A flow control valve 236 regulates system fluid flow at the desired flow rate. As shown in FIG. 2, flow control valve 236 is a pressure-compensated flow-control valve, which internally regulates flow rate independent of system pressure changes. In an alternative embodiment, valve 236 is a standard two-way control valve controlled by an electronic flow controller, using a signal from a flowmeter. Flow control valve 236 displays the fluid flow rate. In a further alternative embodiment, flow control valve 236 is a pressure-compensated flow-control valve, as depicted in FIG. 1, and the flow meter is a mechanical meter with visual indication only.

Heat load 206 receives the fluid, precisely regulated at the desired temperature and flow setpoints, and adds heat to the process fluid, raising its temperature except for when the heat-load is temporarily off. The fluid then returns to reservoir 202.

Figure 3:
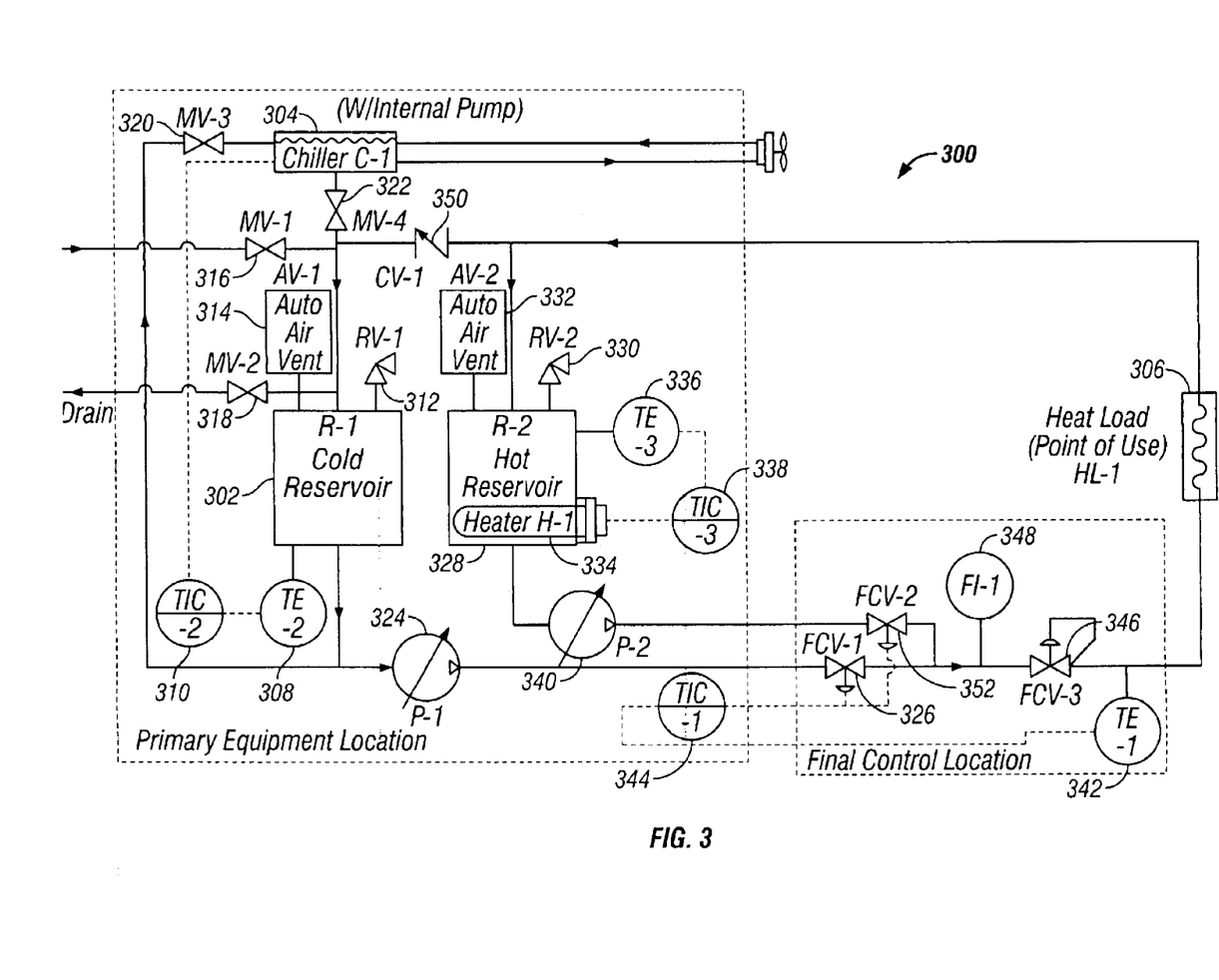
FIG. 3 is a schematic illustration of a temperature control apparatus including two valve fluid mixing.

FIG. 3 is a schematic illustration of a temperature control apparatus 300 for achieving precision temperature control of fluids. A temperature controller 344 compares its setpoint to the value from a sensor 342, and uses that comparison to control the position of flow control valves 326 and 352, which determine the mixing ratio of hot and cold sources from reservoirs 328 and 302. Flow control valves 326 and 352 positions are inversely related; as valve 326 opens, valve 352 closes, and vice versa. The inverse relationship is accomplished with dual signals from controller 344, with one valve being controlled with inverse logic compared to the other.

A cold reservoir 302 contains fluid that is maintained slightly (for example 2° F.) below the final temperature setpoint by a chiller 304. Final temperature setpoint is defined as the temperature desired at a heat load 306. A temperature sensor 308 senses the temperature of cold reservoir 302 and feeds the value to a chiller temperature controller 310. Temperature controller 310 compares its setpoint to the value returned by sensor 308, and controls the amount of cooling provided by chiller 304. Chiller 304 has an internal pump that circulates fluid through cold reservoir 302.

In one embodiment, cold reservoir 302 is equipped with a relief valve 312 to protect from overpressure, and with an automatic air vent 314 to vent excess air. Cold reservoir 302 is sized to provide the appropriate amount of thermal inertia for the system. In an alternative embodiment, apparatus 300 includes manual valves 316, 318, 320, and 322, where valves 316 and 318 are normally closed, while valves 320 and 322 are normally open. These settings are reversed if facility backup cooling is used. A variable displacement pump 324 draws fluid from cold reservoir 302 and delivers it to a first three-way control valve 326. In a further embodiment, a recirculation loop (not shown) to prevent pump overheating, and a circulation pump (not shown) to reduce thermal stratification within cold reservoir 302 is included in apparatus 300.

A hot reservoir 328 is equipped with a relief valve 330 to vent any overpressure, and an automatic air vent 332 to vent excess air. Like cold reservoir 302, hot reservoir 328 is sized to provide the required amount of thermal inertia for the system. Hot reservoir 328 contains fluid that is maintained above (for example 13° F.) the final temperature setpoint by a heater 334. A temperature sensor 336 senses the temperature of hot reservoir 328 and feeds the value to a heater temperature controller 338. Temperature controller 338 compares its setpoint to the value it receives from sensor 336, and from the comparison determines the amount of heating provided by heater 334. A variable displacement pump 340 draws fluid from hot reservoir 328 and delivers it to first three-way control valve 326. In an alternative embodiment, a recirculation loop (not shown) to prevent pump overheating, and a circulation pump (not shown) to reduce thermal stratification within hot reservoir 328 is included in apparatus 300.

A temperature sensor 342 senses the temperature of fluid being delivered to heat load 306, and feeds the value to a final temperature controller 344. Final temperature controller 344 compares its setpoint to the value returned by sensor 342, and controls the position of first three-way control valve 326, which determines the mixing ratio of fluid from hot reservoir 328 and cold reservoir 302.

A second three-way flow control valve 346 regulates system fluid flow at the desired flow rate. Second three-way flow control valve 346 is a pressure-compensated flow-control valve, which internally regulates flow rate independent of system pressure changes. In an alternative embodiment, valve 346 is a standard two-way control valve controlled by an electronic flow controller, through use of a signal from a flow meter 348 which displays the fluid flow rate. In a further alternative embodiment, second three-way flow control valve 346 is a pressure-compensated flow-control valve as depicted in FIG. 3, and the flow meter 348 is a mechanical meter with visual indication only.

Fluid at the desired temperature and flow rate passes to heat load 306, which raises the temperature of the fluid (assuming the heat load is energized). The fluid then returns to cold reservoir 302 and hot reservoir 328, with flow of chilled fluid into hot reservoir 328 prevented if necessary by check valve 350.

Figure 4:
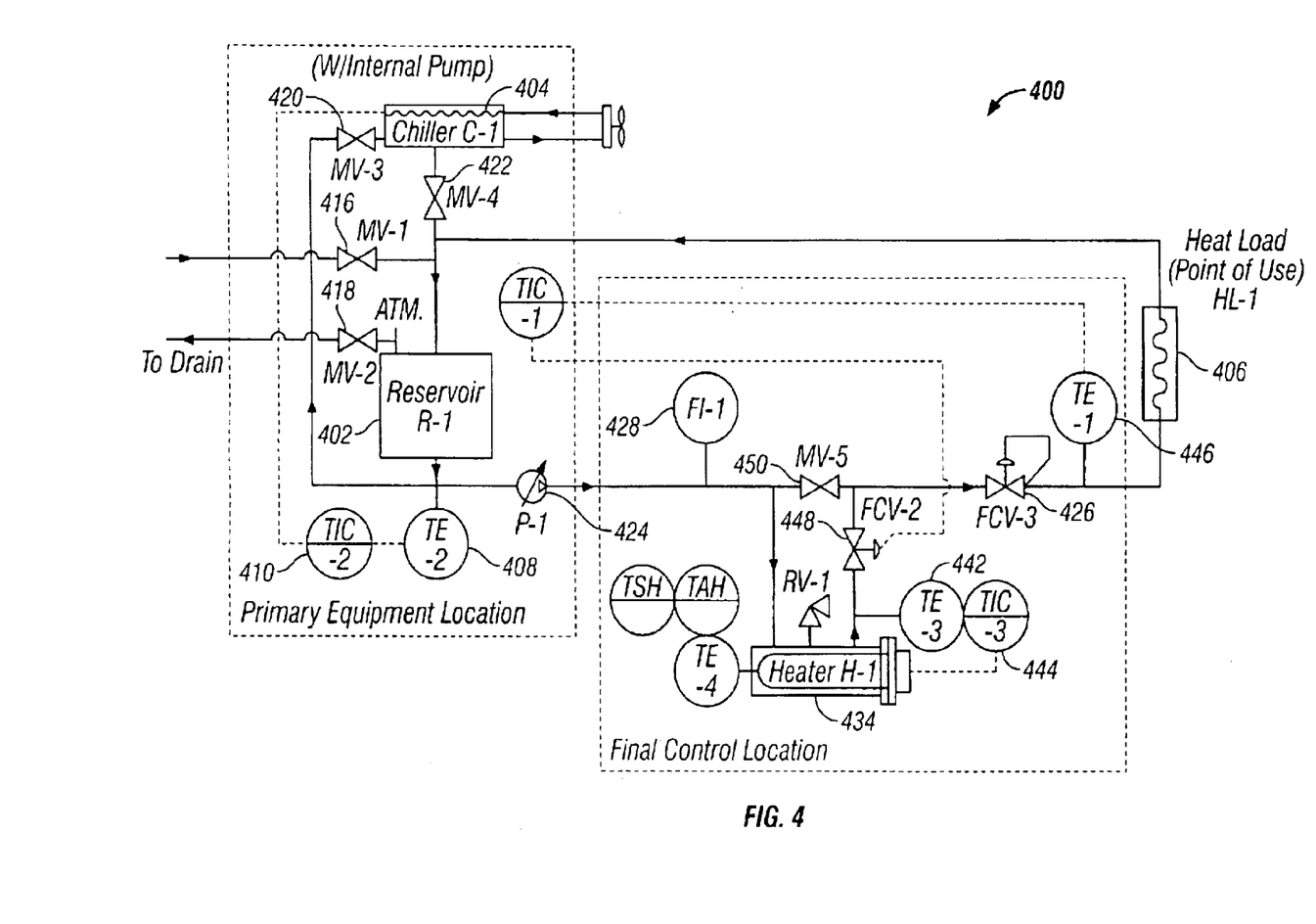
FIG. 4 is a schematic illustration of a temperature control apparatus including a heated bypass loop.

FIG. 4 is a schematic illustration of an apparatus 400 for achieving precision temperature control of fluids. A reservoir 402 contains fluid that is maintained slightly (for example 2° F.) below the final temperature setpoint by a chiller 404. Final temperature setpoint is defined as the temperature desired at a heat load 406. A temperature sensor 408 senses the temperature of reservoir 402 and feeds the value to a chiller temperature controller 410. Chiller temperature controller 410 compares its setpoint to the value returned by temperature sensor 408, and controls the amount of cooling provided by chiller 404. Chiller 404 includes an internal pump that circulates fluid through reservoir 402.

Reservoir 402 is sized to provide the appropriate amount of thermal inertia for the system. In one embodiment reservoir 402 includes a circulation pump to reduce thermal stratification within the reservoir. Manual valves 416 and 418 are normally closed, while manual valves 420 and 422 are normally open. In an alternative embodiment, these settings are reversed if facility backup cooling is used. A variable displacement pump 424 draws fluid from reservoir and delivers it to the final control location.

A flow control valve 426 regulates system fluid flow at the desired flow rate. Flow control valve 426 is a pressure-compensated flow-control valve, which internally regulates flow rate independent of system pressure changes. In one embodiment, this valve is a standard two-way control valve controlled by an electronic flow controller, through use of a signal from a flowmeter. Flowmeter 428 displays the fluid flow rate. In a further alternative embodiment, flow control valve 426 is a pressure-compensated flow-control valve, and flowmeter 428 is a mechanical meter with visual indication only.

A heater 434 contains fluid that is maintained above the final temperature setpoint (for example 13° F.). A temperature sensor 442 senses the temperature exiting heater 434 and feeds the value to a heater temperature controller 444. Heater temperature controller 444 compares its setpoint to the value returned by sensor 442, and controls the amount of heating provided by heater 434.

A temperature sensor 446 senses the temperature of fluid being delivered to heat load 406, and feeds the value to a final temperature controller 444. Final temperature controller 444 compares its setpoint to the value returned by a temperature sensor 446, and controls the position of a flow control valve 448, which determines an amount of hot fluid passing through heater 434 that is mixed with the cold stream that bypasses the heater loop. Flow control valve 448 is set to a position determined by calculation and/or testing that produces a desirable range of flow rates that vary with the position of flow control valve 448. Process fluid precisely regulated at the desired temperature and flow setpoints flows to heat-load 406, where it absorbs heat, and then the fluid returns to reservoir 402. A manual valve 450 forces all fluids to pass through heater 434 and flow control valve 448.

Figure 5:
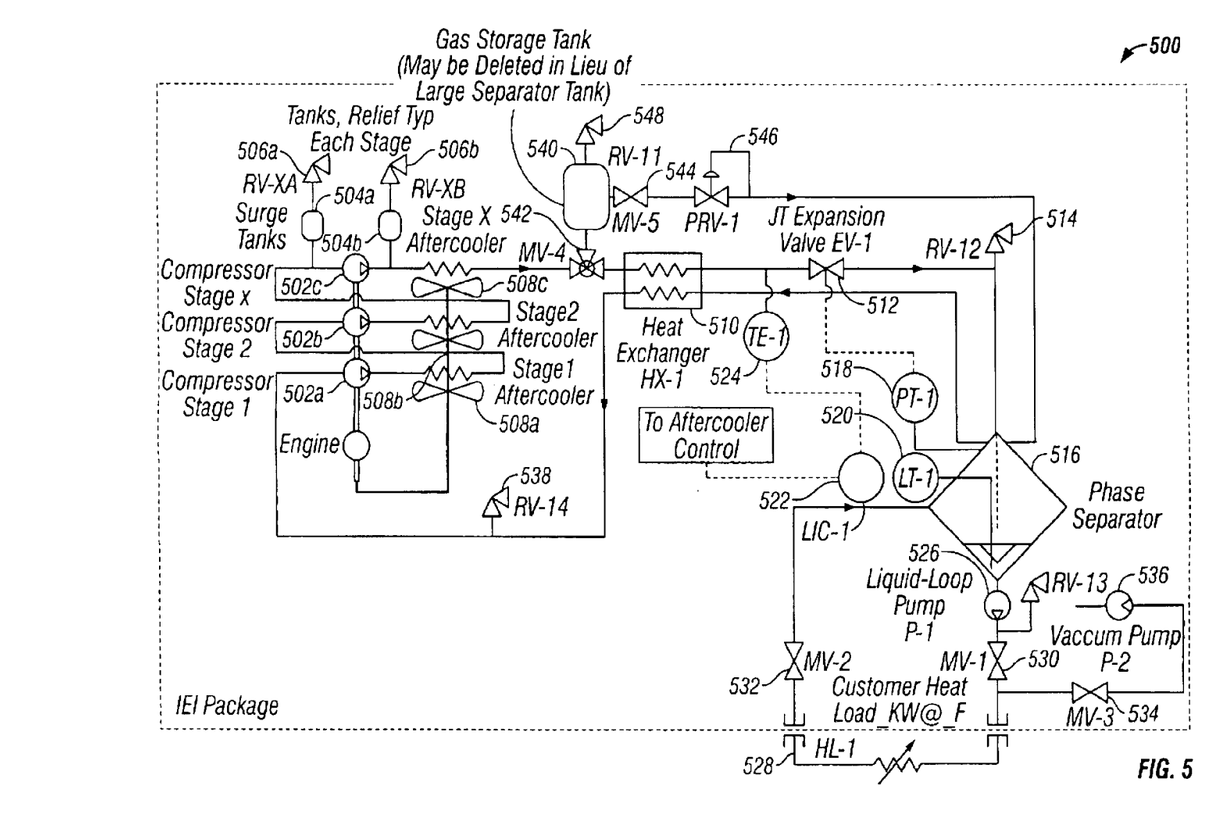
FIG. 5 is a schematic illustration of a temperature control apparatus including a two-phase system.

FIG. 5 is a temperature control apparatus 500 for achieving precise constant temperature across the entire heat-load apparatus. It has a gaseous refrigerant entering a compressor 502, comprising compressor stages 502a, 502b, and 502c. In an exemplary embodiment, compressor 502 comprises multiple stages, as shown in FIG. 5. In one embodiment, compressor 502 is a single or multiple stage unit, piston or centrifugal or other variety, and driven by an electric or diesel motor or other drive mechanism, as is well known in the at. In one embodiment, compressor 502 has surge tanks 504a and 504b with relief valves 506a and 506b. In an alternative embodiment, compressor 502 includes an aftercooler after each compressor stage, so that compressor stage 502a has aftercooler 508a, compressor stage 502b has aftercooler 508b, and compressor stage 502c has aftercooler 508c. In one embodiment, aftercoolers 508a-c is a radiator or other heat exchanger style, cooled by fans, external facility cooling water, or ambient air or other methods well-known in the art. In one embodiment, aftercooler(s) use controls to achieve higher precision depending on system requirements.

The compressed refrigerant then passes through a heat exchanger 510, where it is cooled by the returning saturated vapor refrigerant. Heat exchanger 510 may consist of a condenser rejecting heat to atmosphere or other means of removing heat from the refrigerant, as is well-known in the art. The cooled refrigerant passes through an expansion valve 512, after which the refrigerant exists primarily in the liquid phase. A relief valve 514 protects the phase separator tank and low-pressure side of the system from overpressure.

The refrigerant then enters a phase separator tank 516, where the saturated mixture liquid and vapor phases are separated by gravity, owing to higher density of the liquid phase.

The temperature of the refrigerant in separator tank 516 is controlled to an appropriate temperature setpoint. The primary control loop maintains a constant pressure in phase separator 516. In a two-phase system controlling pressure rather than temperature typically is more accurate because it obviates the lag between a change in the temperature of the refrigerant and that of the temperature sensor, arising from the sensor's thermal inertia. Refrigerant temperature and pressure at saturation are directly related, and hence any change in one will have a precisely known impact on the other. Pressure transmitter 518 senses the separator tank pressure and sends a signal to expansion valve 512, which passes more refrigerant if the pressure drops below the setpoint, and less refrigerant if the pressure rises above the setpoint. The quality, or percentage of liquid vs. vapor, of the refrigerant delivered to the phase separator is controlled to ensure that the phase separator has an appropriate amount of liquid in it. Control of the percentage of liquid vs. vapor is achieved as shown in FIG. 5, where a level transmitter 520 sends a signal to a level controller 522. Level controller 522 also receives a signal from a temperature sensor 524, located near the inlet of expansion valve 512. Level controller 522 also sends a signal to the compressor aftercooler control to alter the percentage of liquid at the compressor aftercooler. A higher liquid percentage eventually delivered to the phase separator tank is obtained by providing additional cooling at the aftercooler. Less cooling at the aftercooler will result in a lower liquid percentage eventually delivered to the phase separator tank. Alternative embodiments employ control methods including but not limited to, direct temperature control in the phase separator tank, control of the compressor outlet pressure by providing a recirculation loop around compressor stage(s), bypass or other variable control of the amount of cooling in heat exchanger 510 or the condenser or other apparatus that performs its basic function.

The liquid refrigerant is pumped by a liquid-loop pump 526 to the point of usage, a heat-load 528, where the heat input vaporizes the refrigerant. Heat-load 528 receives the fluid, precisely regulated at the desired temperature. Precise regulation of flow rate is not as important for two-phase systems as for those achieving temperature control through use of a process fluid that remains in one phase.

In an alternative embodiment, the system is gravity-fed, eliminating the need for pump 526. In one embodiment, manual valves 530 and 532 allow isolation of the customer heat load, while in an alternative embodiment manual valve 534 and vacuum pump 536 allow evacuation of heat load 528 and/or the entire system for startup and maintenance.

Vapor from the separator then travels through the cold side of heat exchanger 510. It enters heat exchanger 510 at point (4V) on FIG. 6, at 31.3 psia and −100° F. It leaves at point (1) on FIG. 6, at 31.3 psia and 100° F. Relief valve 538 protects heat exchanger 510 and the piping from overpressure. The gas then travels back to the compressor inlet, completing the cycle.

Also shown in FIG. 5 is a gas storage tank 540. This is used primarily as a reservoir for refrigerant during system shutdown. Many refrigerants will be gaseous at ambient temperatures, resulting in a high storage pressure. During shutdowns, the position of a manual valve 542 is switched to deliver the refrigerant to the storage tank. A manual valve 544 is closed to contain refrigerant in the tank. When starting up the system, manual valve 544 is opened and pressure reducing valve 546 is set to a value slightly less than the design operating point in order to deliver refrigerant to the system as appropriate. As liquid begins condensing, the pressure drops, drawing more refrigerant into the system. A tank 540 allows much of the system to be designed for low pressure and therefore more economically. Storage 540 is also configured with a relief valve 548.

The example shown differs from standard industrial refrigeration loops in several respects. First, the refrigeration cycle's condensing operation occurs above the vapor dome. This is done primarily to improve efficiency. Secondly, the refrigerant is used both as a refrigerant and as the cooling medium. Typical existing systems for similar applications having such a wide range of cycle temperatures use two or three separate fluids. Multiple fluid systems require much additional apparatus, including separate compressors, resulting in additional expense, maintenance, and inefficiency. Third, heat exchanger 510 allows the refrigerant to cool and heat itself, using returned cold vapor to precool the warm gas, resulting in a significant efficiency improvement.

Figure 6:
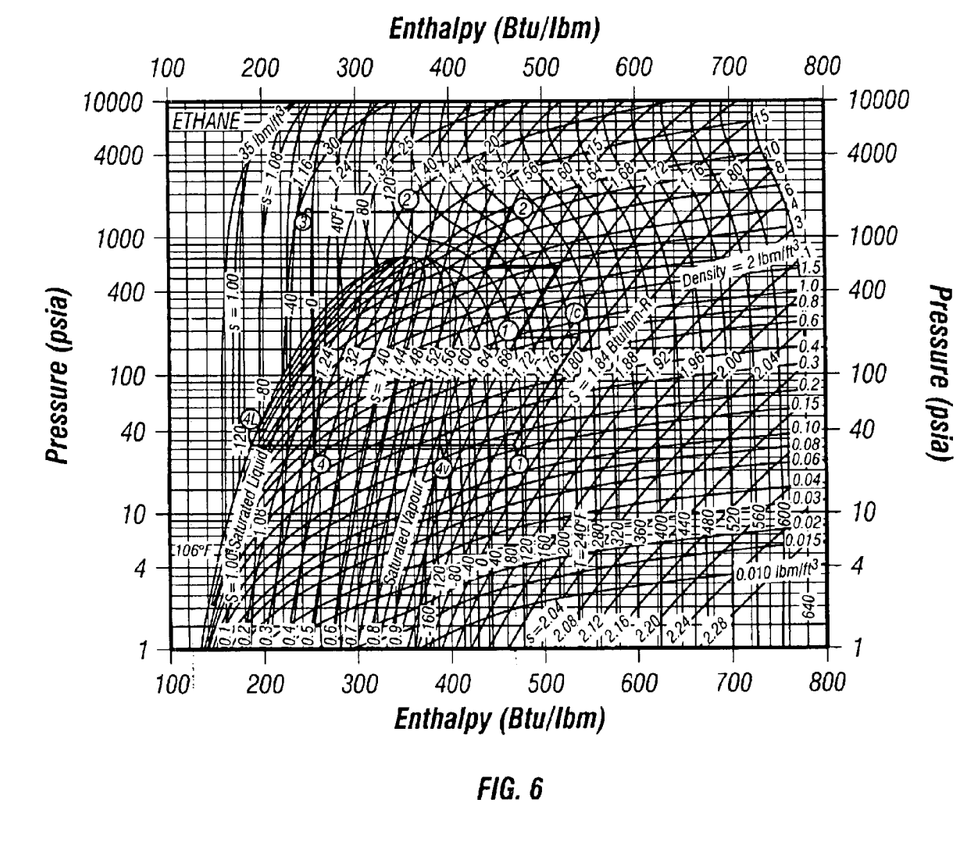
FIG. 6 is a pressure-enthalpy diagram for the two-phase temperature control apparatus of FIG. 5.

FIG. 6 is a pressure-enthalpy (p-h) diagram of a sample refrigeration cycle typically used by temperature control apparatus 500. All design points shown on FIG. 6 are an example only. The pressure and temperature values stated are an example. Particular system requirements and refrigerant selection can result in a wide variation of refrigeration cycle design points.

EXAMPLES

The method of calculating a particular application's required distinct points of resolution is displayed in Design Variation #1, and illustrated in the following sample calculation.

Optimum nominal temperature settings of hot and cold sources are selected. The values depend on the particular application, and may be further optimized by iteration of this calculation procedure. The results of this calculation are one key factor in determining the design variation to be used. Other factors may be important selection criteria for a given application, including facility restrictions, importance of power consumption, and the degree of precision actually required.

$$\text{Flow \%}_{cold} = 100 * (T_{hot} - T_{nom})/(T_{hot} - T_{cold})$$
$$= 100 * (88°\,F. - 75°\,F.)/(88°\,F. - 73°\,F.)$$
$$= 86.67\%$$
$$\text{Flow \%}_{hot} = 100 - \text{Flow \%}_{cold}$$
$$= 100 - 86.67\%$$
$$= 13.33\%$$
$$\text{Flow}_{cold} = \text{Flow}_{total} * (\text{Flow \%}_{cold}/100)$$
$$= 39\,\text{gpm} * (86.67/100)$$
$$= 33.80\,\text{gpm}$$
$$\text{Flow}_{hot} = \text{Flow}_{total} * (\text{Flow \%}_{hot}/100)$$
$$= 39\,\text{gpm} * (13.33/100)$$
$$= 5.20\,\text{gpm}$$
$$\Delta\text{Flow}/\Delta\text{Temp} = [\text{Flow}_{total} * (T_{hot} - (T_{nom} - .01))/(T_{hot} - T_{cold})] - \text{Flow}_{cold}$$
$$= [39\,\text{gpm} * (88°\,F. - (75°\,F. - .01°\,F.))/(88°\,F. - 73°\,F.)] - 33.80\,\text{gpm}$$
$$= 0.0260\,\text{gpm}/.01°\,F.$$
$$\text{Valve Travel \%} = 100 * (\Delta\text{Flow}/\Delta\text{Temp}/\text{Flow}_{cold})$$
$$= 100 * (.0260\,\text{gpm}/.01°\,F./33.80\,\text{gpm})$$
$$= 0.077\%$$
$$\text{Resolution}_{min} - \text{Flow}_{total}/\Delta\text{Flow}/\Delta\text{Temp}$$
$$= 39\,\text{gpm}/.0260\,\text{gpm}/.01°\,F.$$
$$= 1500$$

CONTROL SENSITIVITY

Design Variation #1

| DEVIATION | | TEMP F | | FLOW % | | GPM | | DGPM/.01 MIX | % VALVE TRAVEL | REQUIRED RESOLUTION |
|---|---|---|---|---|---|---|---|---|---|---|
| COLD | HOT | COLD | HOT | COLD | HOT | COLD | HOT | | | |
| NOM/NOM | | 73 | 88 | 86.67 | 13.33 | 33.80 | 5.20 | 0.0260 | 0.077 | 1500 |
| LOW/LOW | | 72 | 87 | 80.00 | 20.00 | 31.20 | 7.80 | 0.0260 | 0.083 | 1500 |
| LOW/HIGH | | 72 | 89 | 82.35 | 17.65 | 32.12 | 6.88 | 0.0229 | 0.071 | 1700 |
| HIGH/LOW | | 74 | 87 | 92.31 | 7.69 | 36.00 | 3.00 | 0.0300 | 0.083 | 1300 |
| HIGH/HIGH | | 74 | 89 | 93.33 | 6.67 | 36.40 | 2.60 | 0.0260 | 0.071 | 1500 |
| | | | | | | | | | | 1700 |

Design Variation #2

| DEVIATION | | TEMP F | | FLOW % | | GPM | | DGPM/.01 MIX | % VALVE TRAVEL | REQUIRED RESOLUTION |
|---|---|---|---|---|---|---|---|---|---|---|
| COLD | HOT | COLD | HOT | COLD | HOT | COLD | HOT | | | |
| NOM/NOM | | 70 | 87 | N/A | N/A | 40.00 | 39.00 | 0.0769 | 0.128 | 780 |
| Flow valve's resolution based on valve sized for 100% open at 60 GPM | | | | | | | | | | 780 |

Design Variation #3

| DEVIATION | | TEMP F | | FLOW % | | GPM | | DGPM/.01 MIX | % VALVE TRAVEL | REQUIRED RESOLUTION |
|---|---|---|---|---|---|---|---|---|---|---|
| COLD | HOT | COLD | HOT | COLD | HOT | COLD | HOT | | | |
| NOM/NOM | | 73 | 88 | 86.67 | 13.33 | 33.80 | 5.20 | 0.0260 | 0.260 | 385 |
| LOW/LOW | | 72 | 87 | 80.00 | 20.00 | 31.20 | 7.80 | 0.0260 | 0.260 | 385 |
| LOW/HIGH | | 72 | 89 | 82.35 | 17.65 | 32.12 | 6.88 | 0.0229 | 0.229 | 436 |
| HIGH/LOW | | 74 | 87 | 92.31 | 7.69 | 36.00 | 3.00 | 0.0300 | 0.300 | 333 |
| HIGH/HIGH | | 74 | 89 | 93.33 | 6.67 | 36.40 | 2.60 | 0.0260 | 0.260 | 385 |
| Hot flow valve's resolution based on valve sized for 100% open at 10 GPM | | | | | | | | | | 436 |

Design Variation #4

| DEVIATION | | TEMP F | | FLOW % | | GPM | | DGPM/.01 MIX | % VALVE TRAVEL | REQUIRED RESOLUTION |
|---|---|---|---|---|---|---|---|---|---|---|
| COLD | HOT | COLD | HOT | COLD | HOT | COLD | HOT | | | |
| NOM/NOM | | 73 | 88 | 86.67 | 13.33 | 33.80 | 5.20 | 0.0260 | 0.260 | 385 |
| LOW/LOW | | 72 | 87 | 80.00 | 20.00 | 31.20 | 7.80 | 0.0260 | 0.260 | 385 |
| LOW/HIGH | | 72 | 89 | 82.35 | 17.65 | 32.12 | 6.88 | 0.0229 | 0.229 | 436 |
| HIGH/LOW | | 74 | 87 | 92.31 | 7.69 | 36.00 | 3.00 | 0.0300 | 0.300 | 333 |
| HIGH/LOW | | 74 | 89 | 93.33 | 6.67 | 36.40 | 2.60 | 0.0260 | 0.260 | 385 |
| Hot flow valve's resolution based on valve sized for 100% open at 10 GPM | | | | | | | | | | 436 |

NOTE:
A low value of required resolution is desirable because it produces higher sensitivity.

Example Calculations for Design Variation #5:
Given: A user must remove 350 kW @ –100° F. from a cold plate. Design ambient condition is 100° F. Based on an analysis of potential refrigerants, ethane is selected due largely to operating at reasonable pressures and a high heat of vaporization.

Design Variation #5

Customer Load = 350 kW

ETHANE          Qcust = 1.19E + 06 Btu/hr

| CYCLE POINT | T (° F.) | P (pisa) | H (Btu #) | liq/vap (mass %) | Dens (#/ft³) |
|---|---|---|---|---|---|
| 1 | 100 | 31.3 | 468 | — | 0.16 |
| 1c | 280 | 175 | 534 | — | — |
| 1' | 120 | 175 | 466 | — | — |
| 2 | 240 | 1500 | 465 | — | — |
| 2' | 120 | 1500 | 346 | — | — |
| 3 | 0 | 1500 | 252 | — | — |
| 4 | –100 | 31.3 | 252 | — | — |
| 4V | –100 | 31.3 | 389 | 0.33 | — |
| 4L | –100 | 31.3 | 187 | 0.67 | 32.7 |
| 5 | (from graph, use h5 below) | | | | 0.88 |

| | | |
|---|---|---|
| Dh (hex cold side) | = | dh (hex warm side) |
| | = | (h2'–h3) |
| | = | 94.0 |
| dh (hex cold side) | = | x(hl–h4 V) + (1 – x)(h1–h5) |
| 94.0 | = | x(hl–h4 V) + (1 – x)(hl–h5) |
| solving for h5 . . . h5 | = | 366.6 |
| solve for quality @ point 5 (shown in table) | | |
| dh (cust load) | = | h5–h4L |
| | | 179.6 |
| dm/dt (liquid loop) | = | Qcust/dh(cust load) |
| | | 6649 #/hr |
| dV/dt (liq loop) | = | dm/dt(liq loop)/60/dens@4 V/ |
| | | .1337 |
| | | 25.3 gpm |
| dm/dt (total) | = | dm/dt(liq loop)/(1 – x) |
| | | 9924 #/hr |
| dV/dt (total) (compressor inlet) | = | dm/dt(total)/60/dens@1 |
| | | 1034 acfm |

While the invention has been described in terms of various specific embodiments, those skilled in the art will recognize that the invention can be practiced with modification within the spirit and scope of the claims.

What is claimed is:

1. An apparatus for supplying fluid at a desired temperature to a heat load, said apparatus comprising:
   a cold reservoir containing fluid at a temperature below the desired temperature;
   a fluid conduit fluidly connected to the cold reservoir; and
   a heated bypass loop comprising a heater, a temperature sensor, a heater temperature controller, and a two-way control valve, said loop fluidly connected to the fluid conduit such that a portion of fluid from said fluid conduit is diverted through said heated bypass loop and then returned to said fluid conduit, said temperature sensor sensing a temperature of the portion of fluid exiting said heated bypass loop and providing such temperature to said heater temperature controller, said heater temperature controller comparing such temperature to a setpoint.

2. An apparatus in accordance with claim 1 further comprising a chiller to chill the fluid in said cold reservoir and a temperature controller to control said heater.

3. An apparatus in accordance with claim 1 wherein said two-way control valve is configured to achieve a temperature control precision at the heat load for the supplied fluid of about ±0.1° F.

4. An apparatus in accordance with claim 1 wherein said fluid conduit comprises a flow control valve to control the flow rate in said fluid conduit.

5. A method of supplying fluid at a desired temperature to a heat load, said method comprising:
   passing a fluid from a cold reservoir containing fluid at a temperature below the desired temperature through a fluid conduit;
   passing at least a portion of the fluid in the fluid conduit through a heated bypass loop which includes a heater, a temperature sensor, a programmable temperature controller and a two-way control valve;
   heating the fluid in the heated bypass loop;
   mixing fluid from the heated bypass loop with fluid from the cold reservoir;
   sensing a temperature of the portion of fluid exiting the heated bypass loop with the temperature sensor; and
   providing such temperature to the programmable temperature controller, the programmable temperature controller controlling the fluid mix to achieve the desired temperature at the heat load with a temperature control precision of about ±0.1° F.

6. A method in accordance with claim 5 further comprising a chiller to chill the fluid in the cold reservoir.

7. A method in accordance with claim 5 wherein the fluid conduit includes a flow control valve.

8. A method for controlling temperature of a fluid at a heat load, the fluid circulating through the heat load at flow rates exceeding five gallons per minute, the temperature of the fluid at the heat load being controlled to within +/–0.1 degree F. of a desired temperature at the heat load, said method comprising:
   providing an amount of fluid that is chilled and maintained at a temperature below the desired temperature at the heat load;
   heating a portion of the fluid to a temperature that is above the desired temperature at the heat load;
   sensing a temperature of the combined chilled and heated fluid being supplied to the heat load;
   routing both the chilled fluid and the heated fluid to the heat load; and
   controlling amounts of chilled fluid and amounts of heated fluid being delivered to the heat load.

9. A method according to claim 8 wherein heating a portion of the fluid to a temperature that is above the desired temperature at the heat load comprises routing a portion of the chilled fluid through a heater.

10. A method according to claim 8 further comprising:
    measuring a temperature of the chilled fluid using a temperature sensor;
    sending the measured temperature to a temperature controller; and
    controlling an amount of chilling applied to the fluid in order to maintain an amount of fluid whose temperature is below the desired temperature at the heat load.

11. A method according to claim 8 further comprising:
    measuring a temperature of the heated fluid using a temperature sensor,
    sending the measured temperature to a temperature controller; and
    controlling an amount of heating applied to the fluid.

12. A method according to claim 8 wherein controlling amounts of chilled fluid and amounts of heated fluid being delivered to the heat load comprises:

sending a temperature of the combined chilled and heated fluid being supplied to the heat load to a controller; and controlling a position of a flow control valve with the controller, the valve controlling an amount of heated fluid and an amount of chilled fluid applied to the heat load.

13. An apparatus for controlling temperature of a fluid at a heat load, said method comprising:

a fluid reservoir configured to maintain a fluid at a temperature below a fluid temperature desired at the heat load;

a first temperature controller for said first fluid reservoir;

a first temperature sensor configured to transmit a temperature of the fluid in said first fluid reservoir to said controller, said controller configured to adjust a temperature of the fluid in said first fluid reservoir;

a fluid heating portion configured to provide fluid at a temperature above a fluid temperature desired at the heat load;

a second temperature controller for said fluid heating portion;

a second temperature sensor configured to transmit a temperature of the fluid in said fluid heating portion to said controller, said controller configured to adjust a temperature of the fluid in said fluid heating portion;

at least one valve configured to let an amount of the chilled fluid and an amount of the heated fluid flow through the heat load;

a third temperature controller for said heat load; and a third temperature sensor configured to transmit a temperature of the fluid at said heat load to said third controller, said controller configured to adjust a setting of said valve to control a mixing ratio of the chilled fluid and the heated fluid to the heat load, the fluid circulating through the heat load at flow rates exceeding five gallons per minute, the temperature of the fluid at the heat load being controlled to within about +/−0.1 degree F. of the fluid temperature desired at the heat load.

14. An apparatus according to claim 13 wherein said heating portion comprises at least one of a hot fluid reservoir, a heat exchanger, and a heating loop.

15. An apparatus according to claim 13 wherein said first fluid reservoir comprises a circulation pump to reduce thermal stratification of the fluid within said reservoir.

16. An apparatus according to claim 13 wherein said controllers are configured with set points, the set point being a desired temperature at a particular location, said controllers configured to return a difference between a measured temperature received from a sensor and a set point temperature for each said controller, said controllers configured to control a position of a flow control valve.

* * * * *